United States Patent [19]
Zhu et al.

[11] Patent Number: 6,004,341
[45] Date of Patent: *Dec. 21, 1999

[54] VASCULAR WOUND CLOSURE DEVICE

[75] Inventors: Yong Hua Zhu, Loma Linda; Wolff M. Kirsch, Redlands, both of Calif.

[73] Assignee: Loma Linda University Medical Center, Loma Linda, Calif.

[ * ] Notice: This patent issued on a continued prosecution application filed under 37 CFR 1.53(d), and is subject to the twenty year patent term provisions of 35 U.S.C. 154(a)(2).

[21] Appl. No.: 08/764,611

[22] Filed: Dec. 5, 1996

Related U.S. Application Data

[60] Provisional application No. 60/009,643, Dec. 7, 1995.

[51] Int. Cl.⁶ .................................................. A61M 29/00
[52] U.S. Cl. ......................... 606/198; 606/191; 606/108; 604/161
[58] Field of Search .................................. 606/108, 185, 606/191, 198, 142; 604/158, 160, 161; 600/201, 208, 219, 220, 222

[56] References Cited

U.S. PATENT DOCUMENTS

| | | |
|---|---|---|
| 1,064,307 | 6/1913 | Fleming ................................. 604/161 |
| 2,566,499 | 9/1951 | Richter ................................... 604/161 |
| 3,518,993 | 7/1970 | Blake . |
| 3,653,388 | 4/1972 | Tenckhoff . |
| 3,774,438 | 11/1973 | Weston . |
| 3,888,117 | 6/1975 | Lewis . |
| 4,064,881 | 12/1977 | Meredith . |
| 4,166,466 | 9/1979 | Jarvik . |
| 4,263,899 | 4/1981 | Burgin . |
| 4,317,445 | 3/1982 | Robinson . |
| 4,325,376 | 4/1982 | Klieman et al. . |
| 4,351,466 | 9/1982 | Noiles . |
| 4,440,170 | 4/1984 | Golden et al. . |
| 4,487,204 | 12/1984 | Hrouda . |
| 4,492,232 | 1/1985 | Green . |
| 4,523,592 | 6/1985 | Daniel . |
| 4,530,698 | 7/1985 | Goldstein et al. . |
| 4,534,351 | 8/1985 | Rothfuss et al. . |
| 4,539,990 | 9/1985 | Stivala . |
| 4,593,693 | 6/1986 | Schenck . |
| 4,610,671 | 9/1986 | Luther . |
| 4,611,595 | 9/1986 | Klieman et al. . |
| 4,616,650 | 10/1986 | Green et al. . |
| 4,622,970 | 11/1986 | Wozniak . |
| 4,651,733 | 3/1987 | Mobin-Uddin . |
| 4,668,221 | 5/1987 | Luther . |
| 4,693,249 | 9/1987 | Schenck et al. . |
| 4,738,658 | 4/1988 | Magro et al. . |
| 4,772,266 | 9/1988 | Groshong . |
| 4,865,593 | 9/1989 | Ogawa et al. . |
| 4,917,087 | 4/1990 | Walsh et al. . |
| 4,921,479 | 5/1990 | Grayzel . |

(List continued on next page.)

FOREIGN PATENT DOCUMENTS

| | | |
|---|---|---|
| 0646350 | 4/1995 | European Pat. Off. . |
| 9202738 | 9/1992 | Germany . |
| 2142244 | 1/1985 | United Kingdom . |
| 9624291 | 8/1996 | WIPO . |
| 9720505 | 6/1997 | WIPO . |

*Primary Examiner*—Michael Buiz
*Assistant Examiner*—Tina T. D. Pham
*Attorney, Agent, or Firm*—Knobbe, Martens, Olson & Bear, LLP

[57] ABSTRACT

A device which facilitates the closure of puncture wounds in the vasculature of a patient is used in conjunction with a guidewire, and helps locate and isolate the site of the puncture wound in the patient. The retractor moves the surrounding tissue laterally when positioned in the patient, and acts as a guide for the physician in locating the exact site of the wound. A double-sleeved balloon can be used in conjunction with the retractor to move the tissues laterally and form a tunnel from the surface of the patient's body to the puncture site. The retractor is preferably used in combination with a surgical clip applicator which delivers clips to the site of the wound, but can also be used with other methods of wound closure such as suturing and stapling.

78 Claims, 8 Drawing Sheets

U.S. PATENT DOCUMENTS

| | | | |
|---|---|---|---|
| 5,099,827 | 3/1992 | Meizer et al. | 128/4 |
| 5,104,394 | 4/1992 | Knoepfler . | |
| 4,930,674 | 6/1990 | Barak . | |
| 4,931,059 | 6/1990 | Cooper . | |
| 4,934,364 | 6/1990 | Green . | |
| 4,961,729 | 10/1990 | Vaillancourt . | |
| 4,984,564 | 1/1991 | Yuen . | |
| 5,015,239 | 5/1991 | Browne . | |
| 5,015,249 | 5/1991 | Nakato et al. . | |
| 5,057,083 | 10/1991 | Gellman . | |
| 5,066,285 | 11/1991 | Hillstead . | |
| 5,139,486 | 8/1992 | Moss . | |
| 5,147,381 | 9/1992 | Heimerl et al. . | |
| 5,176,128 | 1/1993 | Andrese . | |
| 5,176,129 | 1/1993 | Smith . | |
| 5,205,830 | 4/1993 | Dassa et al. . | |
| 5,207,229 | 5/1993 | Winters | 168/772 |
| 5,275,611 | 1/1994 | Behl . | |
| 5,282,827 | 2/1994 | Kensey et al. . | |
| 5,287,714 | 2/1994 | Kramer . | |
| 5,292,311 | 3/1994 | Cope . | |
| 5,300,065 | 4/1994 | Anderson . | |
| 5,306,254 | 4/1994 | Nash et al. . | |
| 5,318,542 | 6/1994 | Hirsch et al. . | |
| 5,320,611 | 6/1994 | Bonutti et al. . | |
| 5,342,373 | 8/1994 | Stefanchik et al. . | |
| 5,360,397 | 11/1994 | Pinchuk . | |
| 5,383,881 | 1/1995 | Green et al. . | |
| 5,383,896 | 1/1995 | Gershony et al. . | |
| 5,397,311 | 3/1995 | Walker et al. | 604/160 |
| 5,407,427 | 4/1995 | Zhu et al. | 604/26 |
| 5,411,520 | 5/1995 | Nash et al. . | |
| 5,417,699 | 5/1995 | Klein et al. . | |
| 5,441,504 | 8/1995 | Pohndorf et al. . | |
| 5,486,195 | 1/1996 | Myers et al. | 606/213 |
| 5,509,893 | 4/1996 | Pracas . | |
| 5,531,744 | 7/1996 | Mardella et al. | 606/48 |
| 5,531,759 | 7/1996 | Kensey et al. . | |
| 5,545,178 | 8/1996 | Kensey et al. . | |
| 5,573,517 | 11/1996 | Bonutti et al. . | |
| 5,577,993 | 11/1996 | Zhu et al. | 600/204 |
| 5,580,344 | 12/1996 | Hasson . | |
| 5,613,948 | 3/1997 | Avellanet . | |
| 5,645,566 | 7/1997 | Brenneman et al. . | |
| 5,649,911 | 7/1997 | Trerotola . | |
| 5,662,681 | 9/1997 | Nash et al. . | |
| 5,674,231 | 10/1997 | Green et al. . | |
| 5,676,689 | 10/1997 | Kensey et al. . | |

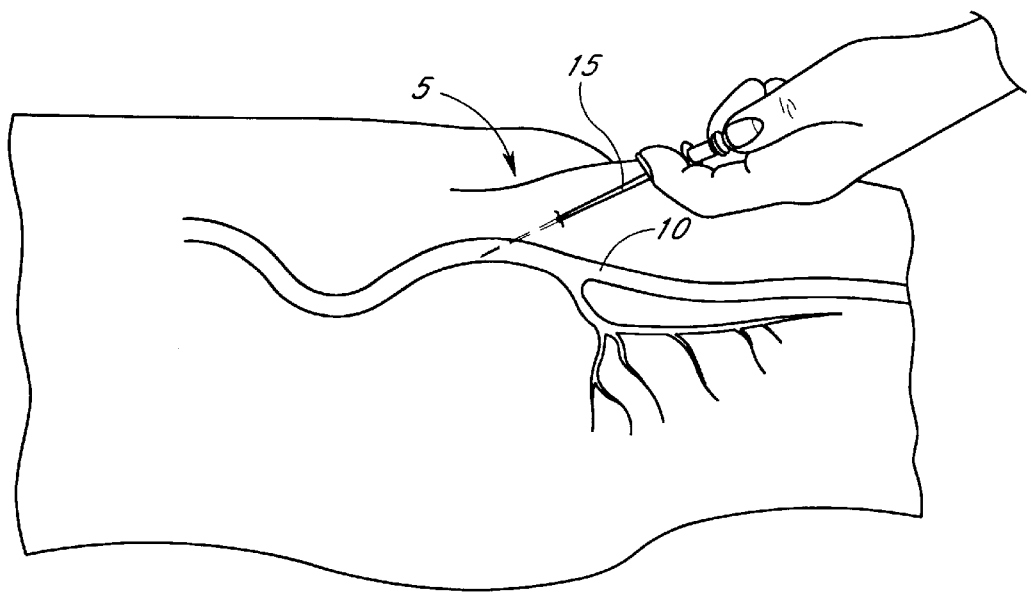
Fig. 1
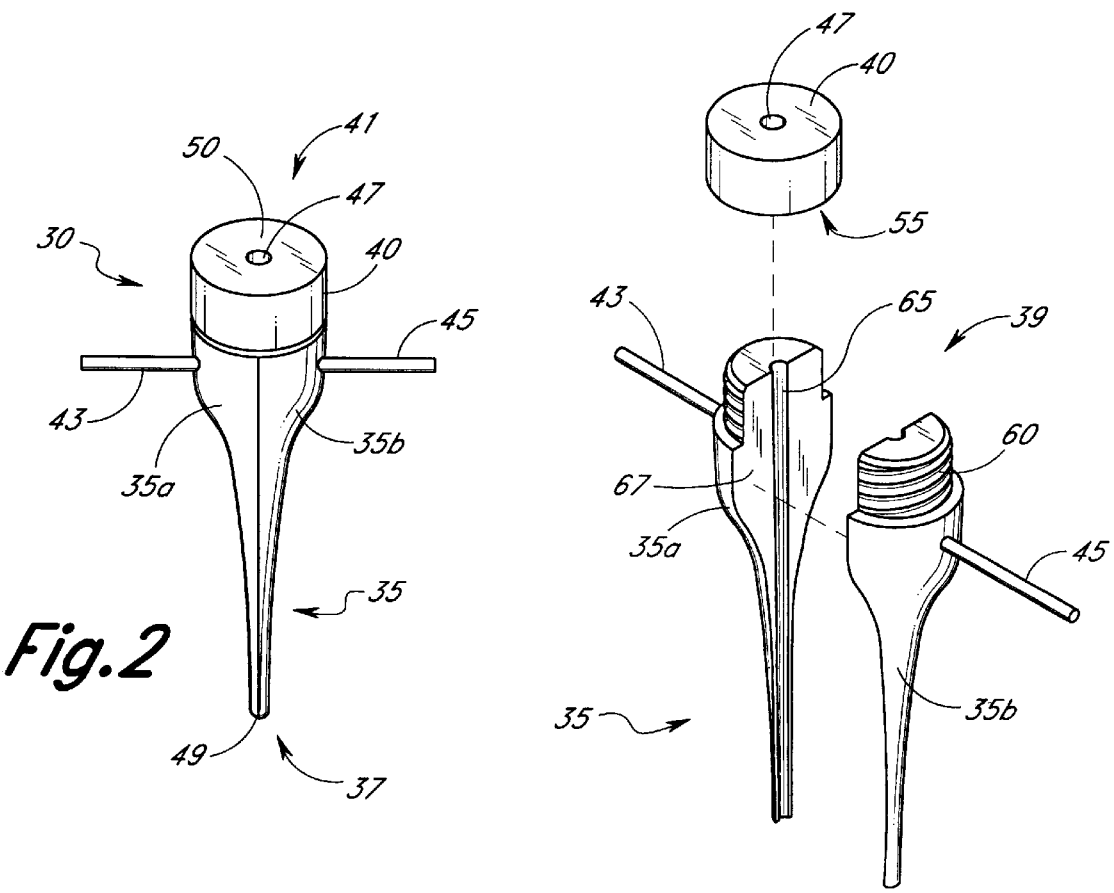
Fig. 2
Fig. 3

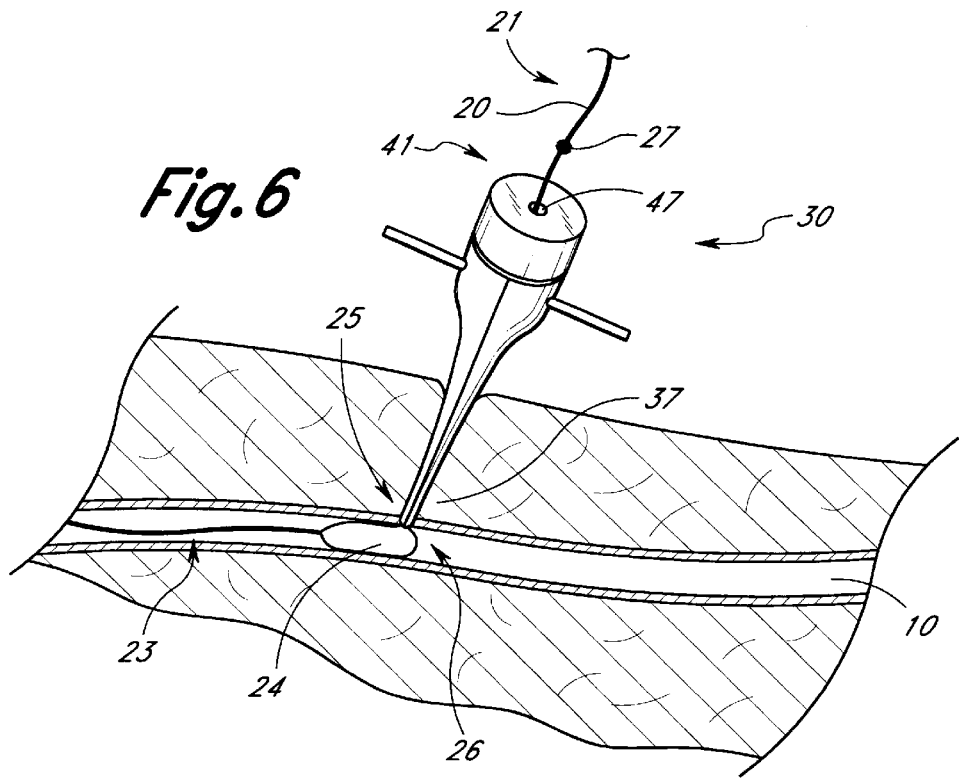
Fig. 6
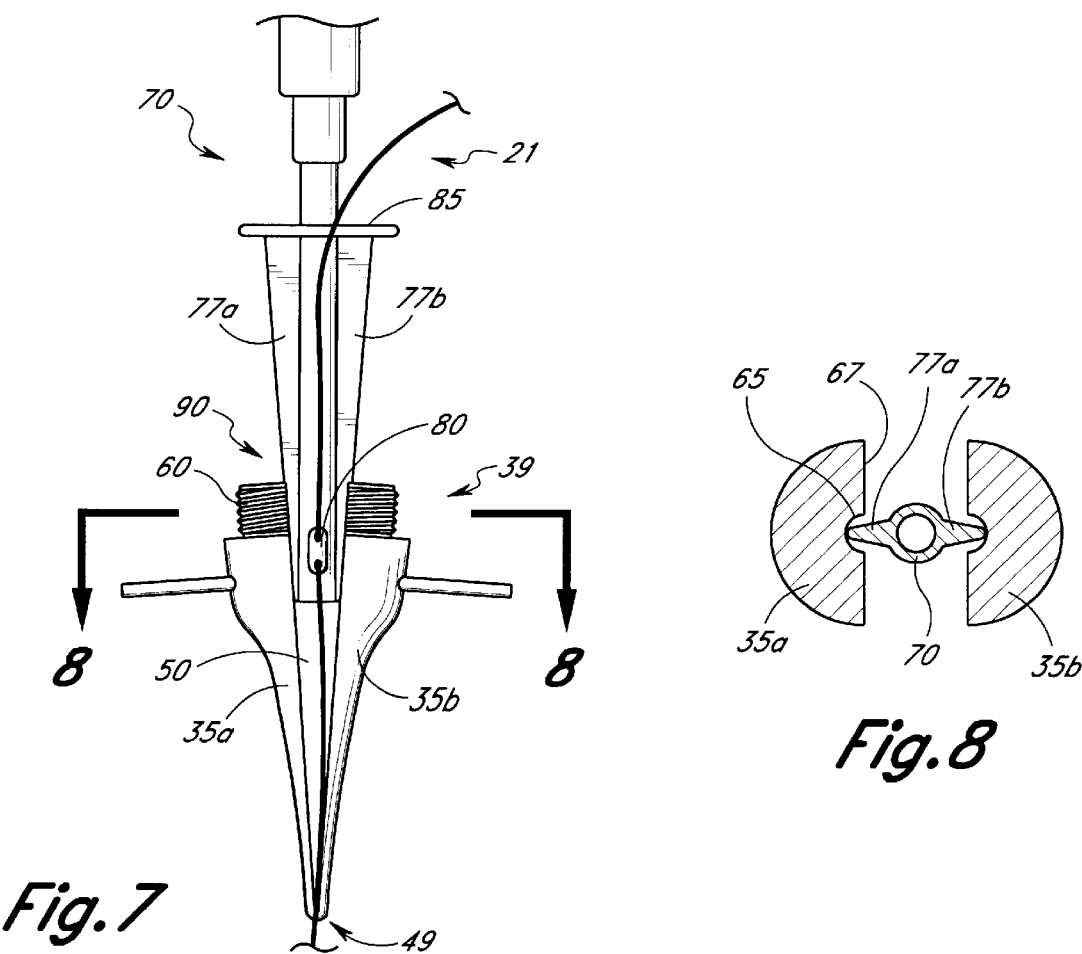
Fig. 7
Fig. 8

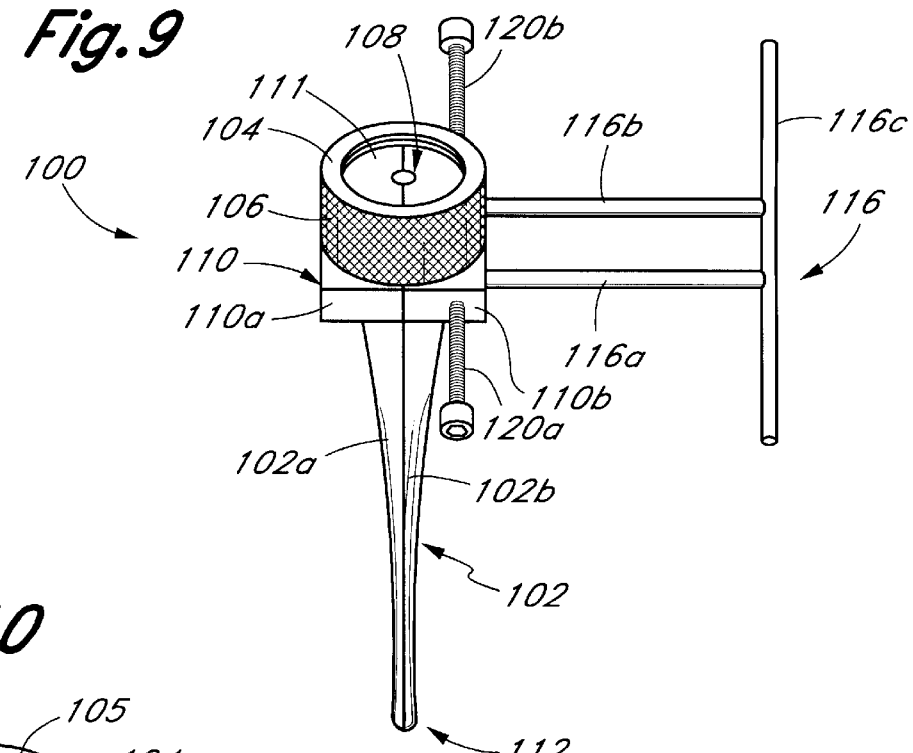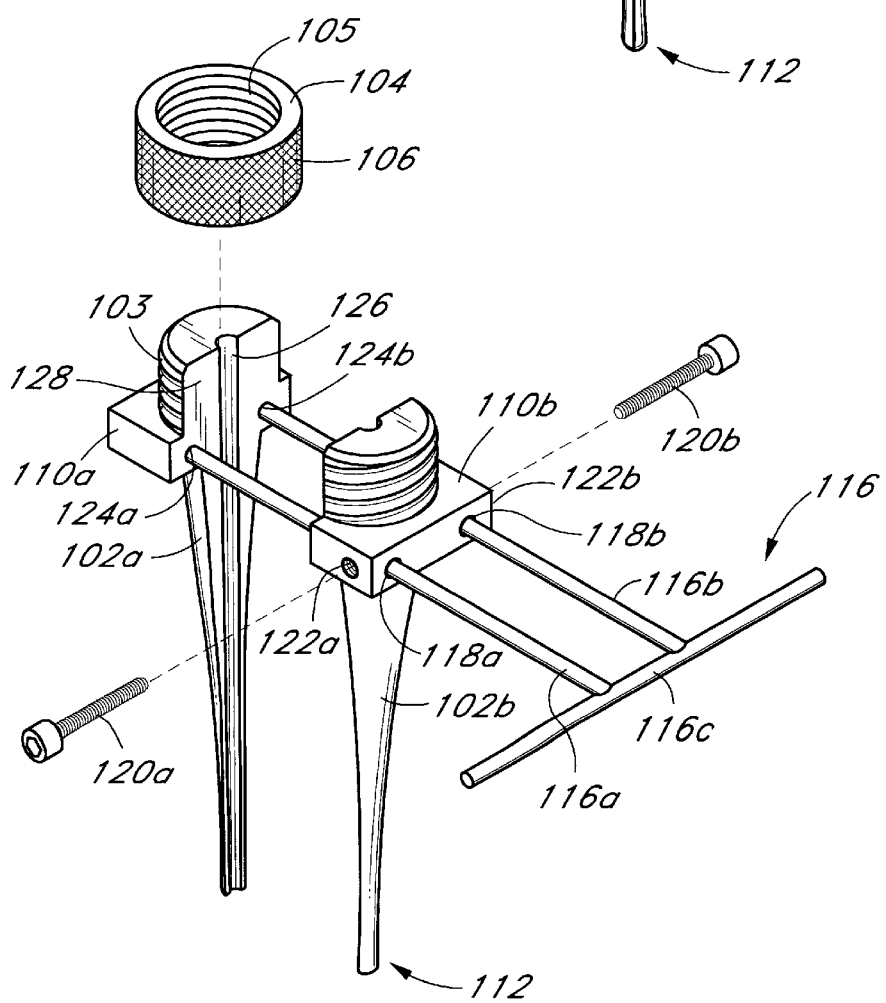

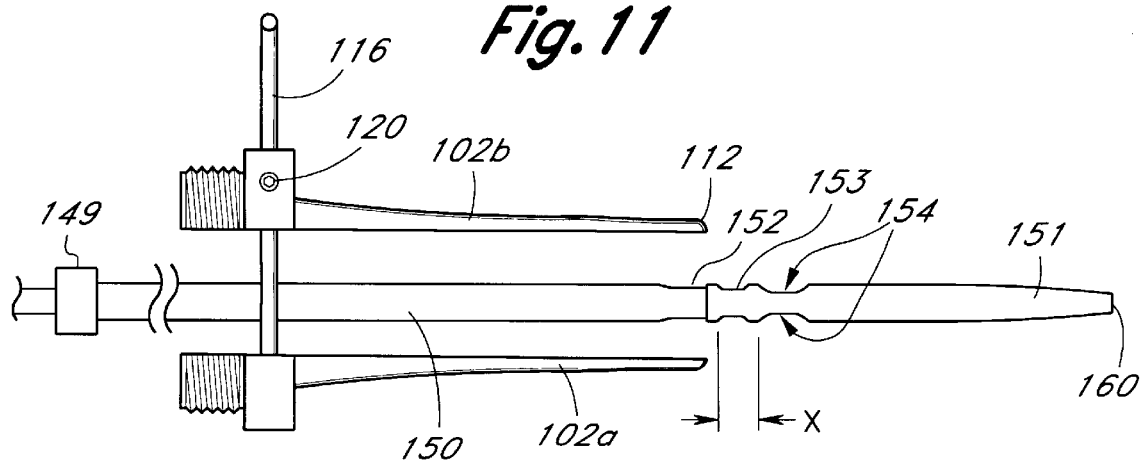
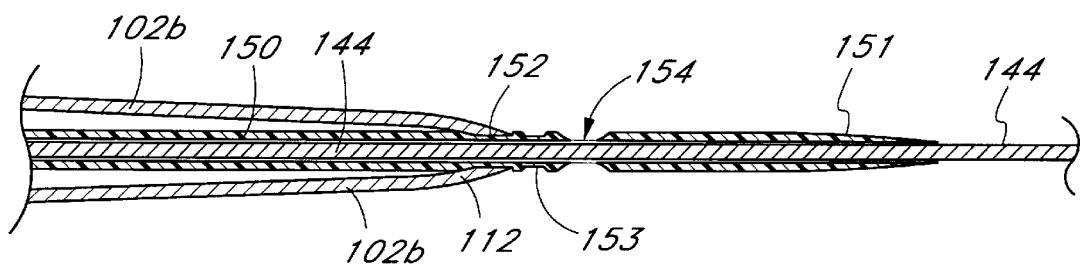
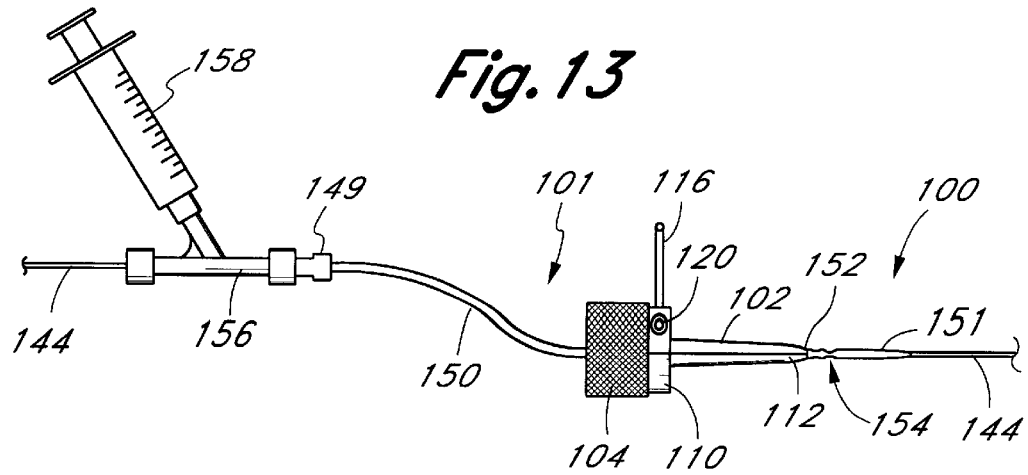

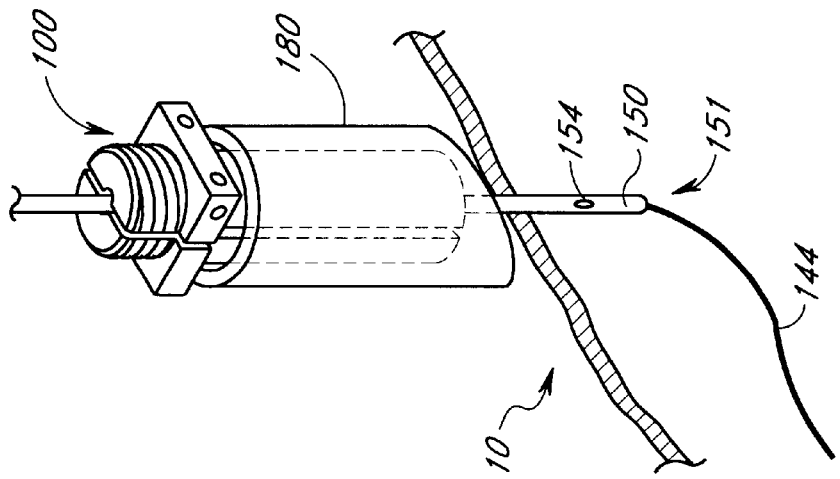
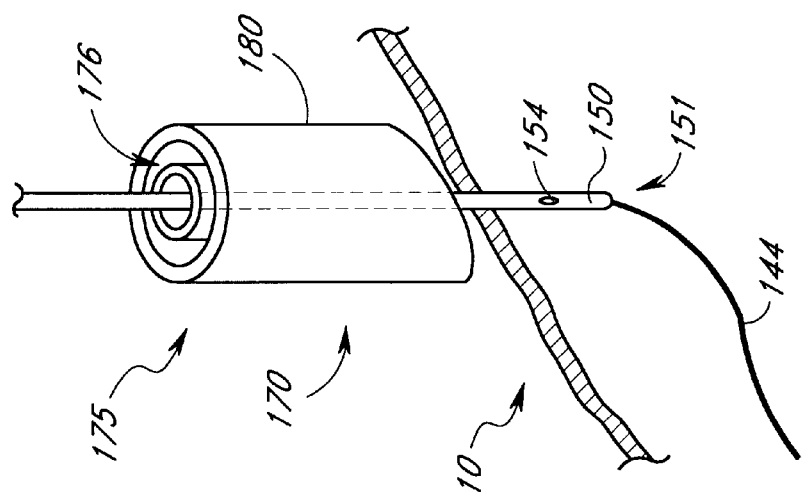
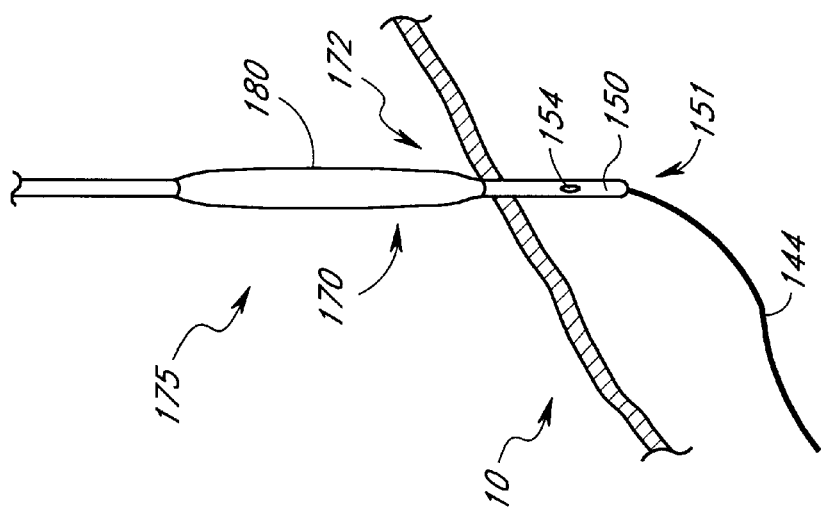

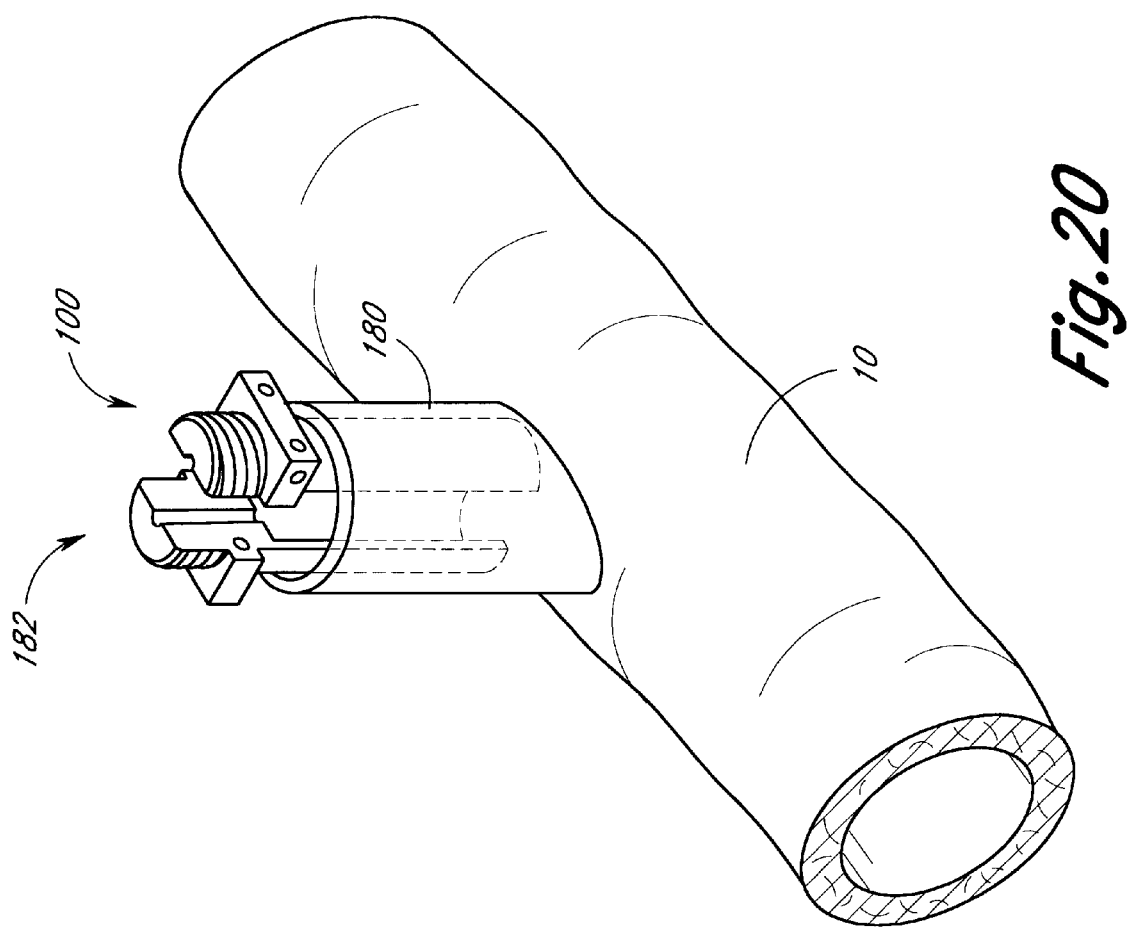

VASCULAR WOUND CLOSURE DEVICE

This application claims priority under 35 U.S.C. §119(e)(1) to provisional application Ser. No. 60/009,643, filed Dec. 7, 1995.

FIELD OF THE INVENTION

The present invention relates to a device to assist in the closure of puncture or other wounds in the vasculature of a patient. Specifically, the invention relates to a vascular wound closure device which aids in locating and isolating the hole in the vasculature and guiding an appropriate wound closure device to the site, so that the wound may be closed using surgical clips, sutures, or staples.

BACKGROUND OF THE INVENTION

Transluminal balloon angioplasty is used in the treatment of peripheral vascular disease to increase or restore blood flow through a significantly narrowed artery in a limb; it is also used in the treatment of blockage of the coronary arteries. In fact, coronary angioplasty has emerged as a major viable alternative to bypass surgery for revascularization of stenotic and occluded coronary arteries. Unlike bypass surgery, angioplasty does not require general anesthesia, opening of the chest wall, use of a heart-lung machine, or transfusion of blood. Angioplasty is not only less invasive and less traumatic to the patient, it is also less expensive because of the shorter hospital stay and shorter recovery time.

Transluminal balloon angioplasty is performed by first inserting a hollow needle through the skin and into the patient's femoral artery. A guidewire is advanced through the hollow needle and into the artery, then along the patient's vasculature toward the site of the blocked blood vessel or heart valve to be treated. X-ray imaging is used to help move the guidewire through the vascular system and into position just past the stenosis to be treated. A balloon catheter is then threaded over the guidewire and advanced until the deflated balloon is within the stenosis. The balloon is then repeatedly inflated to widen the narrowed blood vessel. After the procedure is complete, the catheter and guidewire are withdrawn from the blood vessels and the patient.

Angiography, which is used to detect diseases that alter the appearance of blood vessels, is performed in a similar manner. A hollow needle is first inserted through the skin and into the femoral artery, and a guidewire is then inserted through the needle and into the affected blood vessel. A catheter is then threaded over the guidewire and into the blood vessel to be examined, using x-ray imaging to guide the catheter to the desired position. Contrast medium is then injected, and a rapid sequence of x-ray pictures are taken so that blood flow along the affected vessel can be studied. Once complete, the catheter and guidewire are removed from the patient's body.

After the catheter and guidewire used during angioplasty or angiography are removed, the puncture wound in the femoral artery must be closed and the bleeding through the puncture site in the artery stopped. Currently, ice packs and pressure are applied to the artery for a period lasting up to several hours in an attempt to stop the bleeding. Although efforts have been made to close the puncture wound using staples, clips, and sutures, they have been unsuccessful, largely due to the inability to clearly locate and visualize the puncture wound in the femoral artery.

Other wounds in the vasculature of a patient can also be difficult to locate and access. Thus, a device and method to facilitate the closure wounds in the vasculature of a patient, such as femoral artery puncture wounds following transluminal balloon angioplasty and angiography, would be extremely beneficial. A device having the ability to aid in locating the puncture wound and facilitating the closure of the wound using staples, clips, or sutures would eliminate the prolonged bleeding currently associated with such wounds.

SUMMARY OF THE INVENTION

The wound closure device of the present invention aids in locating and isolating a puncture wound in the vasculature of a patient. It is used in conjunction with a guidewire which is normally inserted into the vasculature during diagnostic and therapeutic procedures. The device of the present invention aids the physician in closing the wound, thus eliminating prolonged bleeding associated with these procedures.

In accordance with one aspect of the present invention, there is provided a device to facilitate the closure of wounds in the femoral artery. The device comprises a body portion having an externally threaded proximal end and a tapered distal end. The body portion is separable into two halves, each of the halves having a flat internal surface with a groove therein, such that when said internal surfaces abut one another, the grooves form a channel through the body portion. The retractor also comprises an internally threaded cap having a hole therethrough. The internal threads are adapted to engage the external threads on the body portion, such that when the cap engages the body portion, the hole is positioned directly above the channel in the body portion, forming one continuous channel that runs the length of the retractor.

In one embodiment of the present invention, the device further comprises at least one handle located on the proximal end of the body portion and extending laterally from the body portion. The body portion and the cap are preferably comprised of a biocompatible engineering polymer, such as polypropylene, polyethylene, or polyterephthalate. The body portion and the cap can also be comprised of an elastomer. Most preferably, the body portion and the cap are comprised of a metal, such as stainless steel.

In another embodiment of the present invention, the device further comprises a guidewire. The guidewire is inserted through the channel in the body portion and through the hole in the cap. Preferably, the guidewire has an inflatable balloon attached near its distal end.

In accordance with another aspect of the present invention, there is provided a system for facilitating the closure of wounds in the vasculature of a patient. The system comprises a retractor having a body portion with an externally threaded proximal end and a tapered distal end. The body portion is separable into two halves, each of the halves having a flat internal surface with a groove therein, such that when the internal surfaces abut one another, the grooves form a channel through the body portion. The retractor also comprises an internally threaded cap having a hole therethrough. The internal threads are adapted to engage the external threads on the body portion, such that when the cap engages the body portion, the hole is positioned directly above the channel in the body.

The system further comprises a guidewire having an inflatable balloon attached thereto. The guidewire is inserted through the channel in the body portion and through the hole in the cap. A surgical clip applicator having a distal end fitted with two laterally protruding wings is also used. The wings are adapted to fit within the channel in the body portion of the retractor. The surgical clip applicator further comprises a guide attached to the distal end of the applicator and extending laterally therefrom. The guide is adapted to receive the guidewire through its ends.

In accordance with yet another aspect of the present invention, there is provided a method for facilitating the closure of a wound in the vasculature of a patient. The method comprises the steps of inserting a guidewire having a proximal end and a distal end and an inflatable balloon into the vasculature through the wound, until the distal end of the guidewire is within the vasculature and the proximal end remains outside the patient's body; inflating the inflatable balloon; withdrawing the proximal end of the guidewire from the patient's body until the inflated balloon is located in the vasculature at the site of the wound; and inserting the proximal end of the guidewire into a distal end of a retractor. The proximal end of the guidewire is inserted in the retractor until the proximal end emerges through a hole in the cap. The method further comprises the steps of advancing the retractor along the guidewire and into the patient's body until the distal tip of the retractor contacts the inflated balloon; removing the cap from the body portion of the retractor; separating the two halves of the retractor until the wound is visible; and closing the wound. The closing step preferably comprises either clipping, stapling, or suturing the wound.

In a preferred method, a surgical clip applicator is inserted into the retractor body portion after the cap is removed. The clip applicator is advanced through the channel in the body portion until the applicator contacts the wound. The closing step preferably comprises applying at least one surgical clip to the wound.

The method preferably further comprises the step of deflating the balloon and withdrawing the guidewire from the patient's body prior to the closing step.

In accordance with still another aspect of the present invention, there is provided another method for facilitating the closure of wounds in the vasculature of a patient. This method comprises the steps of inserting a guidewire having a proximal end and a distal end into the vasculature through the wound, until the distal end of the guidewire is within the vasculature and the proximal end remains outside the patient's body; inserting a catheter having a proximal end and a distal end and having an inflatable balloon attached at the distal end, into the vasculature over the guidewire until the distal end is within the artery and the proximal end remains outside the patient's body; inflating the inflatable balloon; withdrawing the catheter from the patient's body until the inflated balloon is located in the vasculature at the site of the wound; and inserting the proximal end of the guidewire and catheter into the distal end of a retractor. The guidewire and catheter are advanced as a unit until the proximal end of the guidewire emerges through the hole in the cap of the retractor.

The method further comprises the steps of advancing the retractor along the guidewire and catheter and into the patient's body until the distal tip of the retractor contacts the inflated balloon; removing the cap from the body portion of the retractor; separating the two halves of the retractor until the wound is visible; withdrawing the catheter from the patient but leaving the guidewire to guide the wound closure device to the site of the wound; and removing the guidewire and closing the wound. The closing step preferably either clipping, stapling, and suturing the wound.

In a preferred embodiment, the method further comprises the steps of inserting a surgical clip applicator into the retractor body portion after the cap is removed, and advancing the clip applicator over the guidewire and through the channel in the body portion until the applicator contacts the wound. The closing step preferably comprises applying at least one surgical clip to the wound.

In yet another preferred embodiment, the method of the present invention further comprises the step of deflating the balloon and withdrawing the catheter and the guidewire from the patient's body prior to the closing step.

In still another preferred embodiment of the present invention, there is disclosed a device to facilitate the closure of wounds in the vasculature of a patient. The device comprises a body portion having an externally threaded proximal end and a tapered distal end. The body portion is separable into two halves, each having a flat internal surface with a groove therein, such that when the internal surfaces abut one another, the grooves form a channel through the body portion. The device also comprises a collar portion distal the externally threaded proximal end comprising at least one guide passage which traverses both halves of said body portion; at least one pin insertable into the guide passage; and an internally threaded annular cap. The internal threads are adapted to engage the external threads on the body portion. The device may also include a handle extending laterally from the pin, and at least one set screw hole in the collar portion at a right angle to the guide passage, and at least one set screw.

The device also preferably comprises a hollow dilator having an open proximal end and an open distal end adapted to receive a guidewire therethrough. The dilator can be inserted through the channel in the body portion and through the annular cap. The dilator further comprises a notch near the distal end sized to receive the tapered distal end of the device. The dilator preferably has at least one indicator hole through a side wall located distal the notch. A pressure sensor can also be mounted on the outside wall of the dilator.

In a preferred embodiment, a guidewire is inserted through the hollow dilator. The hollow dilator has an open proximal end and an open distal end adapted to receive a guidewire therethrough, and the dilator can be inserted through the channel in the body portion and through the annular cap. The hollow dilator may also include a double-sleeved inflatable balloon mounted on its distal end, and at least one indicator hole. The double-sleeved inflatable balloon is mounted approximately 1.5 mm proximal the indicator hole.

The device is preferably comprised of a biocompatible engineering polymer, such as polypropylene, polyethylene, or polyterephthalate, or an elastomer, or a metal, such as stainless steel.

In accordance with yet another aspect of the present invention, there is provided a system for facilitating the closure of wounds in the vasculature of a patient. The system includes a retractor, a hollow dilator adapted to receive a guidewire therethrough, and a guidewire. A guide assembly which is adapted for attachment to the distal end of a surgical clip applicator can also be used. The assembly comprises a guide plate which is reversibly attachable to a guide body having an attached guide tube sized to receive a guidewire. The guide plate has two laterally protruding wings attached, which are adapted to fit within the channel in the retractor.

The system preferably also includes a source of negative pressure attached to the proximal end of the dilator, such as a syringe. A Y-connector having a plurality of ports can also be attached to the proximal end of the dilator, and a source of negative pressure attached to one of the ports of the Y-connector.

In accordance with still another aspect of the present invention, there is provided a method for facilitating the closure of a wound in the vasculature of a patient. The method comprises the steps of inserting a proximal end of a hollow dilator having a notch formed near its distal end into a distal end of a retractor comprising a body portion having an externally threaded rounded proximal end, and a tapered distal end; mounting the retractor on the dilator so that the distal tapered end is positioned within the notch on the dilator; inserting a guidewire into the vasculature of the patient through the wound; inserting the proximal end of the guidewire into the distal end of the dilator having the retractor mounted thereon until the proximal end of the guidewire emerges through the proximal end of the dilator; advancing the dilator and retractor along the guidewire and into the patient's body, while providing a source of negative pressure on the dilator until blood is drawn into the dilator from the vasculature; removing the cap from the retractor and separating the two halves of the retractor; removing the guidewire and dilator from the patient's body; and closing the wound.

The wound can be closed by clipping, stapling, or suturing. Preferably, the method further includes the steps of attaching to the distal end of a surgical clip applicator a guide having laterally extending wings, inserting the wings into the retractor body portion and advancing the clip applicator through the channel in the retractor until the applicator contacts the wound. At least one surgical clip is then applied to the wound.

The guide preferably includes a guidetube for receiving the guidewire, and the method further comprises inserting the proximal end of the guidewire through the guidetube. The applicator is advanced over the guidewire and through the channel in the retractor until the applicator contacts the wound.

In accordance with still another aspect of the present invention, there is provided a method for facilitating the closure of a wound in the vasculature of a patient, comprising the steps of inserting a guidewire into the vasculature through the wound until the distal end of the guidewire is within the vasculature and the proximal end remains outside the patient's body; inserting the proximal end of the guidewire into a hollow dilator having a double-sleeved balloon mounted on its distal end; advancing the dilator over the guidewire into the vasculature, which is indicated by blood being aspirated through the dilator, which indicates that the wound has been reached; inflating the double-sleeved balloon; inserting the guidewire and dilator into the retractor; advancing the retractor between the two sleeves of the double-sleeved balloon until the distal end reaches the distal detachable junction of the two sleeves; removing the cap from the retractor; separating the two halves of the retractor and removing the dilator and the inner sleeve of the double-sleeved balloon therethrough, leaving the guidewire in place to guide a wound closure device to the wound, the outer sleeve of the balloon forming a tunnel from the surface of the body to the wound; removing the guidewire and closing the wound. The closing of the wound can be done by clipping, stapling, and suturing.

Preferably, the method includes the steps of attaching to a distal end of a surgical clip applicator a guide having laterally extending wings, inserting the wings into the retractor after the cap is removed and advancing the clip applicator through the channel in the retractor until the applicator contacts the wound. At least one surgical clip is then applied to the wound.

The guide preferably further comprises a guidetube for receiving the guidewire, and the method further comprises inserting the proximal end of the guidewire through the guidetube and advancing the applicator over the guidewire and through the channel in the retractor until the applicator contacts the wound.

The claimed method also preferably includes providing a source of negative pressure on the dilator until blood is drawn into the dilator from the vasculature, during the advancing of the dilator over the guidewire.

BRIEF DESCRIPTION OF THE DRAWINGS

FIG. 1 is a side view of a portion of a human body, showing the site where the femoral artery is typically accessed and punctured during angioplasty or angiography.

FIG. 2 is a perspective view of one embodiment of the wound closure device of the present invention.

FIG. 3 is an exploded perspective view of the wound closure device of the present invention.

FIG. 6 is a partial cross-sectional view of a portion of a human body, showing the femoral artery having a guidewire positioned therein, and a perspective view of the retractor of the present invention positioned over the guidewire, with its distal tip at the site of the puncture in the femoral artery.

FIG. 7 is a side view of the retractor with its cap removed and the wings of the surgical clip applicator inserted into the grooves within the retractor.

FIG. 8 is a cross-sectional view of the clip applicator and retractor taken along line 8—8 in FIG. 7.

FIG. 9 is a perspective view of an alternate embodiment of a femoral artery closure device in accordance with the present invention.

FIG. 10 is an exploded perspective view of the alternate embodiment of the femoral artery closure device illustrated in FIG. 9.

FIG. 11 is a side view of the 2 halves of the retractor of FIGS. 9 and 10 separated slightly and having a dilator inserted therethrough.

FIG. 12 is a cross-sectional view of the distal end of the retractor having a dilator and a guidewire inserted therethrough.

FIG. 13 is a side view of the components of the femoral artery localization and closure assembly.

FIG. 17 is an enlarged perspective view of a dilator having a removable double-sleeved balloon at its distal end.

FIG. 18 is an enlarged perspective view of the dilator of FIG. 17 with the sleeves of the balloon inflated.

FIG. 19 is an enlarged perspective view of the dilator of FIG. 18 having an alternate embodiment of a retractor inserted between the sleeves of the balloon.

FIG. 20 is an enlarged perspective view of the dilator and retractor of FIG. 19 with the dilator removed, illustrating the tunnel formed by the retractor and the outer sleeve of the balloon.

DETAILED DESCRIPTION OF THE PREFERRED EMBODIMENT

Introduction

Although the description which follows details the closure of a puncture wound in a femoral artery, the present invention is not intended to be limited to use only with the femoral artery. Rather, the description which follows is exemplary only, and those of skill in the art can readily modify the method described below to use with other types of wounds to the vascular system.

Figure 4:
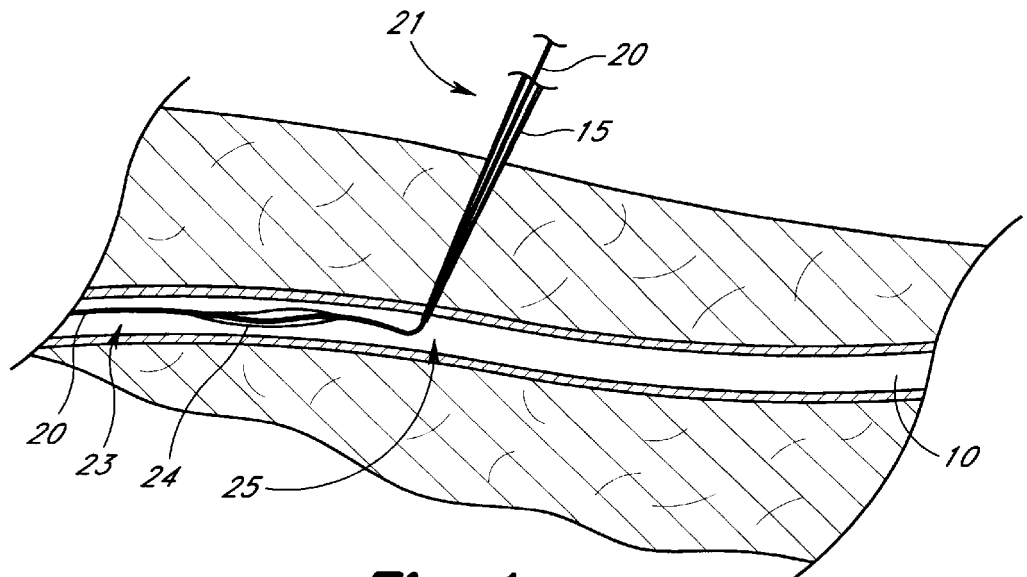
FIG. 4 is a cross-sectional view of a portion of a human body, showing the femoral artery accessed via a hollow needle, and a guidewire having an inflatable balloon attached, inserted through the hollow needle and into the femoral artery.

Referring first to FIG. 1, there is shown a side view of a portion of a human body, showing a site 5 where a femoral artery 10 is typically accessed and punctured during angioplasty or angiography. During these procedures, a hollow needle 15 is first inserted through the skin and into the femoral artery 10. A guidewire 20 is then inserted through the proximal end of the hollow needle 15 and into the artery 10, as illustrated in FIG. 4, and the needle 15 is withdrawn from the patient. The guidewire 20 is advanced through the patient's vasculature, often using x-ray imaging as an aid in directing the guidewire 20 to the desired location.

Once the guidewire 20 is in the desired location, a catheter is used. The proximal end of the guidewire 21 is inserted into the distal end of the catheter, and the catheter is threaded over the guidewire 20 and advanced to the desired location. In the case of angioplasty, the catheter has an inflatable balloon attached at its distal end. Once in position within the stenosis, the balloon is repeatedly inflated and deflated to widen the narrowed blood vessel. In the case of angiography, a catheter is threaded over the guidewire 20 as just described and into the blood vessel to be examined. Contrast medium is then injected, and a rapid sequence of x-ray pictures are taken so that blood flow along the affected vessel can be studied.

After either of these procedures is completed, the catheter and guidewire 20 are withdrawn from the blood vessel and the patient. The puncture wound 25 in the femoral artery 10 caused by the insertion of the hollow needle 15, guidewire 20 and catheter must be closed and the bleeding through the puncture site 25 in the artery 10 stopped.

Construction of the Retractor

In order to facilitate the closure of the wound 25 in the femoral artery 10, a retractor 30 is employed. The retractor 30, illustrated in FIGS. 2 and 3, comprises a body portion 35 and a cap 40. The body 35 of the retractor 30 has a narrow, tapered distal end 37, and a broader circular proximal end 41. The device 30 has two handles 43, 45 located on its body 35, one on each half 35a, 35b. The handles 43, 45 are positioned approximately one-third of the way from the proximal end of the retractor 41, and extend laterally from the body of the retractor 35. These handles 43, 45 assist the user in handling the device 30. The retractor 30 also comprises a circular cap 40 at its proximal end 41, having a hole 47 therethrough. This hole 47 extends into a channel 50 which runs the entire length of the device 30.

As illustrated in FIG. 3, the cap 40 and body 35 of the retractor 30 comprise three separable pieces: the cap portion 40 and the two halves of the body portion 35a, 35b. The removable cap 40 is internally threaded 55. The proximal end 39 of the two halves of the body 35a, 35b are externally threaded 60, and are adapted to removably receive the cap 40. Each half of the body of the retractor 35a, 35b has a semi-circular groove 65 on its flat internal surface 67. When the cap 40 is securely screwed onto the two halves of the body 35a, 35b as illustrated in FIG. 2, the three pieces are joined together, and the semi-circular grooves 65 form a channel 50 running through the interior of the device 30, which starts at the hole in the cap 47 at the proximal end 41 and continues through the body 35, ending at a small hole 49 in the distal end of the retractor 37 where the two halves of the body 35a, 35b come together. When the cap 40 is unscrewed from the body 35, the two halves of the body 35a, 35b may be moved apart from one another, as illustrated in FIG. 3.

Alternate Embodiment of the Retractor

Another preferred embodiment of the invention is illustrated in FIGS. 9–10. In this embodiment, the retractor 100 includes a retraction mechanism whereby the two halves 102a, 102b of the retractor body 102 can be moved apart from one another a desired distance, while maintaining their alignment. The retractor again comprises a body portion 102, and an annular cap 104. The two halves 102a, 102b of the body are initially held together by the internally threaded 105 cap 104. This cap 104 is screwed on and off the externally threaded halves 102a, 102b of the retractor body. The outer surface of the cap 106 can be textured to ease hand tightening and loosening of the cap 106. As illustrated in FIG. 10, each half 102a, 102b of the retractor body again has a semicircular groove 126 running longitudinally down the center of its flat internal surface 128. When the cap 104 is securely screwed onto the two halves 102a, 102b of the retractor body, such that the internal surfaces 128 abut one another, the semicircular grooves 126 form a channel 108. The cap 104 is open on both ends and through its center to permit access to the channel 108.

The retractor 100, as illustrated in FIGS. 9–10, further comprises a collar 110 located on the retractor body 102 just distal to the externally threaded proximal end 103; a pin assembly 116, comprising two parallel pins 116a, 116b attached at one end to a perpendicular handle 116c and at the other end to one half of the retractor body 102a at points 124a and 124b; and two set screws 120a, 120b. As illustrated in FIG. 10, the pins 116a, 116b traverse guide passages 118a, 118b bored through the collar region 110b of one half 102b of the retractor body, such that one half 102b of the retractor body can slide apart from the other half 102a on the pins 116a, 116b. The collar 110b includes internally threaded holes 122a, 122b adapted to receive externally threaded set screws 120a, 120b. The set screw holes 122a, 122b enter the collar region 110a at right angles to the pin guide passages 118a, 118b, such that when the set screws 120a, 120b are advanced, they tighten upon the pins 116a, 116b and thus, fix the distance between the two halves 102a, 102b of the retractor body.

As illustrated in FIGS. 11–13, the retractor 100 is preferably used in conjunction with a dilator 150. As is known to those of ordinary skill in the art, the hollow dilator 150 preferably includes a standard male connector 149, such as a Luer connector, at its proximal end and is narrowly tapered at its distal end 151. The inside diameter of the dilator channel 160 is large enough to accommodate a guidewire 144, so that the dilator 150 can be fed along the guidewire 144 and into the lumen of the femoral artery. Dilators are commonly used in procedures such as angioplasty and angiography to enlarge the puncture site and provide improved access to the femoral artery. In accordance with the present invention, the dilator is preferably notched 152, near its distal end 151 around its entire circumference. Notch 152 provides a seat for the tapered distal tips of the two halves 102a, 102b of the retractor body, such that when the retractor 100 is closed upon the dilator 150, the sharp distal tip of the retractor body 112 is buried in the notch 152 of the dilator. This forms a smooth transition between the dilator 150 and retractor 100 (FIG. 12). Notch 154 provides a groove in which the wall of the femoral artery rests when the dilator has been properly positioned. As will be explained more fully below, when the guidewire 144 is inserted through the dilator 150 and the dilator 150 is then inserted through the retractor 100, (FIGS. 12–13), the dilator 150 lies securely within the interior circular channel 108 (FIG. 9) running the length of the retractor body 102.

The dilator 150 also preferably includes at least one indicator hole 154. The dilator 150 illustrated in FIGS. 11–13 includes two indicator holes 154 (FIGS. 11–12), directly opposed to one another, located a few millimeters distal to the notch 152. The distance X between the holes 154 and the notch 153 is preferably only slightly larger than the thickness of the wall of the femoral artery. Alternatively, a transducer-tipped pressure monitoring catheter, mounted to the outside of the dilator 150, may be used in conjunction with the dilator 150 and indicator holes 154. Use of the indicator holes 154 and pressure sensor will be described in detail below.

A preferred embodiment of the present invention comprising an entire femoral artery localization and closure assembly is illustrated in FIG. 13. The guidewire 144 which emerges from the original puncture wound is fed through the dilator 150, and then the dilator 150 is inserted through the retractor 100. The retractor 100 is mounted on the dilator 150 such that the distal tips of the retractor 112 rest within the notch 152 in the dilator 150. Preferably, the male fitting 149 on the proximal end of the dilator 150 is connected to one port of a commercially available 3-way Y-connector 156. A syringe 158 or other means of applying negative pressure is connected to one of the other ports on the Y-connector 156 and the proximal end of the guidewire 144 exits the Y-connector 156 via the remaining port. The Y-connector 156 therefore acts as a seal at the proximal ends of dilator 150 and guidewire 144.

In an alternate preferred embodiment of the invention, a modified dilator and retractor are used. As illustrated in FIG. 17, a double-sleeved balloon 170 is removably attached to the dilator 150 near its distal end 151, proximal the indicator hole 154. Preferably, the balloon 170 is placed a distance from the indicator hole 154 which is approximately the width of the arterial wall, e.g., 1.5 mm. The inflatable, double-sleeved balloon 170 is angled at its distal end 172 to allow the balloon to fit the femoral artery 10. The balloon 170 includes inflation means which allow the balloon to be inflated and deflated. The retractor 100, rather than having a tapered distal tip as described above, has a cylindrical distal end. This shape prevents the retractor 100 from entering the artery during insertion. Use of the double-sleeved balloon 170 and the cylindrical retractor 100 will be described in detail below.

The retractor of the present invention is preferably formed of one of many strong, biocompatible engineering polymers. Plastics such as polypropylene, polyethylene, or polyterephthalate, are preferred. Elastomers such as silastics or silicones can also be used. Most preferably, metals such as stainless or surgical steel, or titanium are used to form the retractor.

The Surgical Clip Applicator

Figure 5:
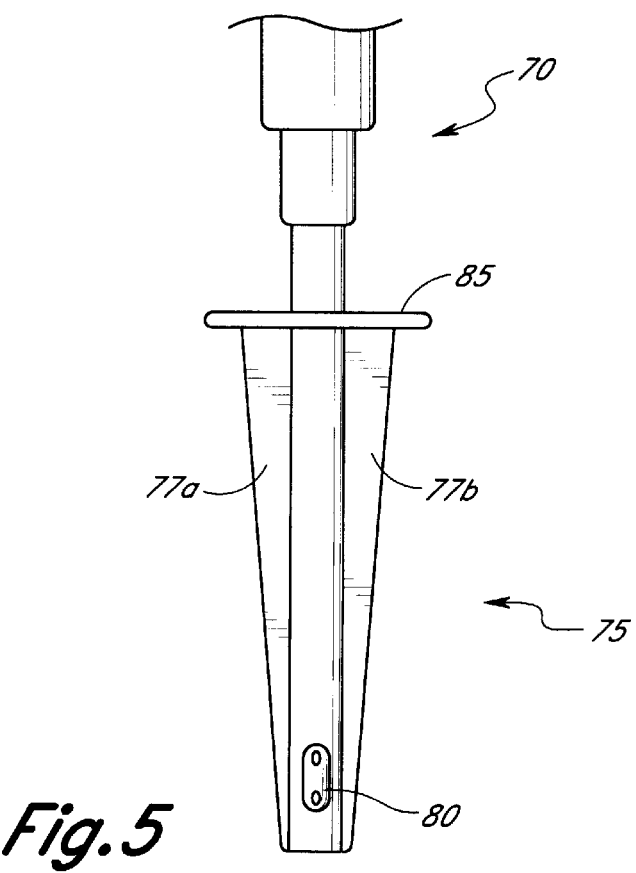
FIG. 5 is a side view of the distal end of a surgical clip applicator to be used in conjunction with the wound closure device of the present invention.

The retractor of the present invention is used to facilitate closure of wounds to the vasculature of a patient using surgical clips, staples, and sutures. One aspect of the present invention therefore includes the use of a surgical clip applicator 70. A surgical clip applicator 70 for use with the retractor 30 of the present invention is illustrated in FIG. 5. As shown in this figure, the distal end of the clip applicator 75 is fitted with two triangular protrusions or wings 77a, 77b that extend laterally from the sides of the distal end of the clip applicator 75. These wings 77a, 77b are configured to fit within the grooves 65 located on the interior surface of the two halves 35a, 35b of the body of the retractor 30, as is best seen in FIG. 8. With the wings 77a, 77b of the clip applicator 70 in the grooves 65 in the two halves of the body of the retractor 35a, 35b, the clip applicator 70 is guided into proper position within the patient's body, as will be discussed in more detail below. In addition, the surgical clip applicator 70 preferably has a guide 80 attached to its distal end 75. The guide 80 preferably extends laterally from the side of the clip applicator 70, and is open at its proximal and distal ends such that a guidewire 20 may be threaded therethrough. This guide 80 is used in combination with the guidewire 20 to accurately guide the clip applicator 70 to the site of the vascular puncture 25, as will be described below.

The surgical clip applicator 70 preferably also has a stop 85 located proximal of the distal end 75, at the point where the proximal ends of the wings of the applicator 77a, 77b end. As will be explained, the stop 80 also aids in the proper positioning of the clip applicator 70 at the site of the vascular puncture 25, and prevents the clip applicator 70 from being inserted too far into the patient's body.

Figure 14:
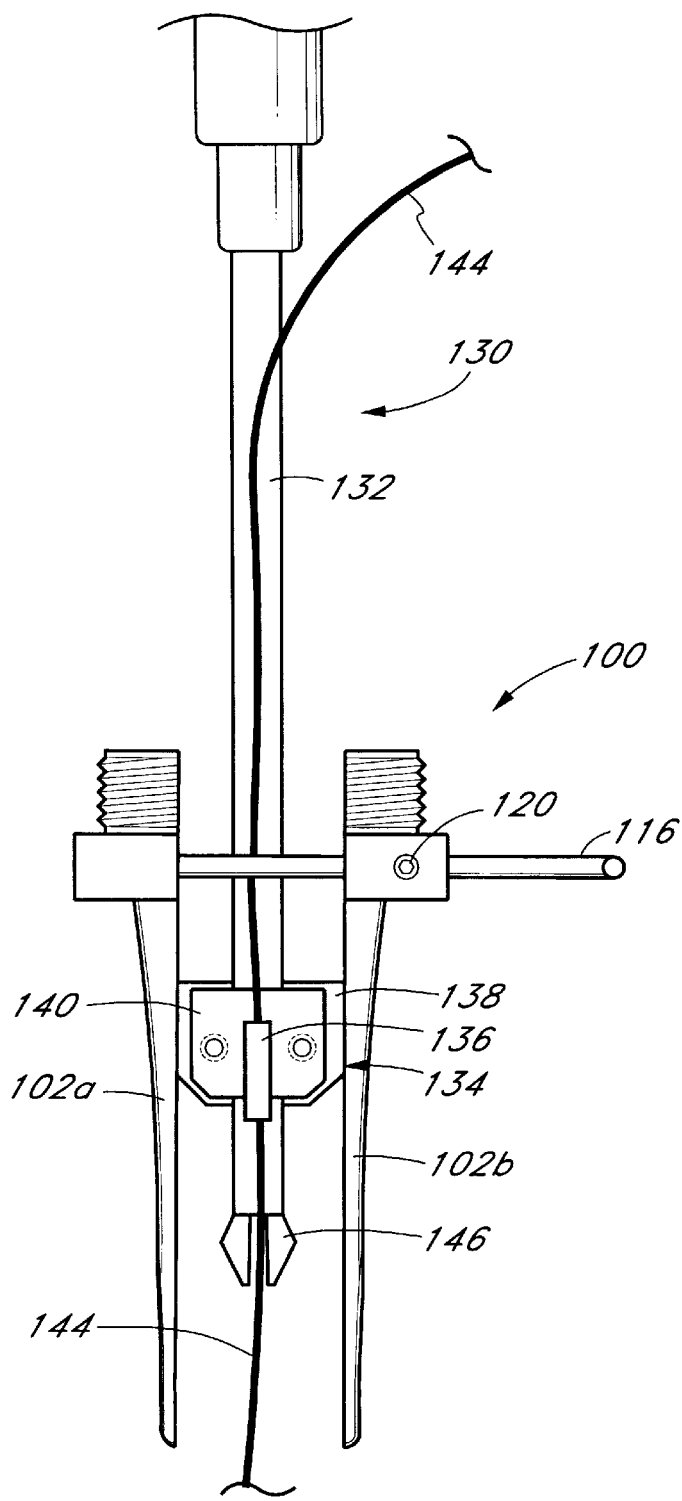
FIG. 14 is a side view of the 2 halves of the retractor separated slightly and having a surgical clip applicator with an applicator guide and a guidewire inserted therethrough.
Figure 15:
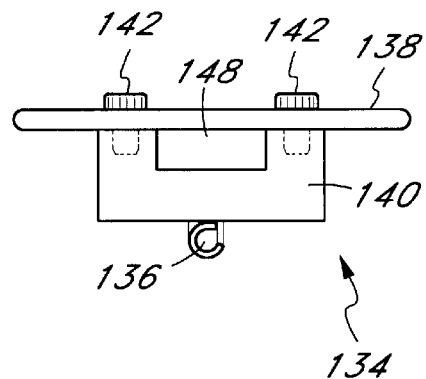
FIG. 15 is a top view of the surgical clip applicator guide of the present invention.
Figure 16:
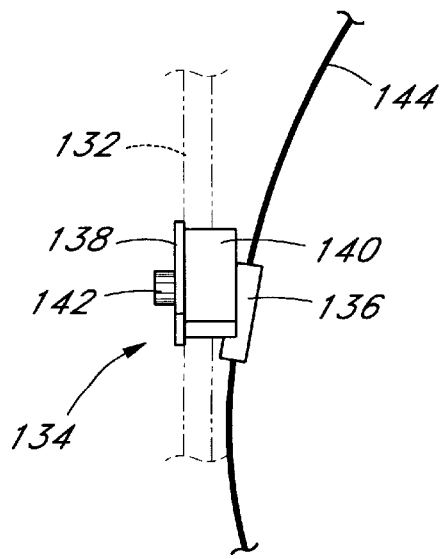
FIG. 16 is a side view of the clip applicator guide, having a guidewire inserted therethrough.

Referring now to FIGS. 14–16, there is illustrated an alternate preferred embodiment of a surgical clip applicator assembly 130. The clip applicator assembly 130 incorporates a standard commercially available surgical clip applicator 132. In accordance with the present invention, the applicator is modified to include a guide assembly 134 reversibly fastened near its distal end. The guide assembly comprises a winged guide plate 138 which is reversibly secured to a body 140. In the embodiment illustrated in FIGS. 14–16, allen screws 142 are used to attach the guide plate 138 but other well known means of attachment can also be used. The distal end of the surgical clip applicator 132 slides within the channel 148 (FIG. 15) formed when the winged guide plate 138 is fastened to the guide body 140.

Attached to the guide body 140 is a guidetube 136 which is adapted to accept the guidewire 144. A preferred embodiment of said guidetube 136 includes a mechanism to close the guidetube 136 once the guidewire 144 has entered. Such a mechanism may involve a second partially open tube which fits within said guidetube 136. This second tube can be rotated within the guidetube 136 to open the guidetube 136 when the openings in both tubes are aligned or close the guidetube 136 when the openings of the tubes are offset. To facilitate the opening and closing, the inner tube preferably includes a handle that passes through a slot in the outer guidetube 136. This mechanism can be spring-loaded like the closures commonly used on pieces of jewelry.

The surgical clip applicator guide assembly 134, together with the retractor 100 and the guidewire 144, is designed to accurately guide the clip applicator 132 to the site of the femoral artery puncture as detailed below. As explained above, the lateral edges of the winged guide plate 138 are configured to fit within the groove 126 (FIG. 10) located on the interior surface of each half of the retractor body 102a, 102b. The surgical clip applicator 132 is guided between the retracted halves of the retractor body 102a, 102b following the guidewire 144 which passes through the guidetube 136 at the distal most end of the surgical clip applicator 132.

Method of Use

Referring first to FIGS. 4–8, the method of use of the retractor 30 in conjunction with a surgical clip applicator 70 to close a wound 25 in the femoral artery 10 will now be described. As noted above, during angioplasty or angiography, the femoral artery 10 is first punctured with a hollow needle 15 and a guidewire 20 is inserted therethrough (FIG. 4). A proximal portion of the guidewire 21 remains outside the patient's body. After the distal end of the guidewire 23 is in position within the femoral artery 10, the hollow needle 15 is removed. A catheter (not shown) is then threaded over the guidewire 20, and inserted into the patient's body.

In a preferred embodiment, a specially designed guidewire 20 having an inflatable balloon 24 located near its distal end 23 is used for the diagnostic or therapeutic procedure. The guidewire 20 is threaded through the hollow needle 15 and into the patient's vasculature. Alternatively, such as for balloon angioplasty procedures, a standard guidewire well known to those of skill in the art can be used in conjunction with a balloon catheter. The balloon on the distal end of the catheter can be used in place of the balloon 24 located on the guidewire 20.

Following completion of the therapeutic or diagnostic procedure, the catheter used during the procedure is removed. The guidewire 20 remains in place in the patient's vasculature. (Note that when a balloon catheter is used in places of a guidewire having a balloon on its distal end, the catheter is left inside the patient, and use of its balloon is identical to the use of the balloon 24 on the guidewire 20 described below).

When the physician desires to close the wound 25 in the femoral artery 10, he or she first withdraws the guidewire 20 and/or catheter through the patient's vasculature using the portion of the guidewire 20 and/or catheter that remains outside the patient's body 21, until the distal end 23 of the guidewire 20 and/or catheter is within the femoral artery 10 close to the femoral artery puncture site 25. The balloon 24 on the distal end 23 of the guidewire 20 or catheter is then inflated, and the guidewire 20 or catheter is withdrawn further until the physician feels some resistance. This will indicate that the balloon 24 is inside the femoral artery 10 and at the site of the puncture wound 25. The physician then threads the proximal end of the guidewire 21 into the hole 49 located at the distal end 37 of the fully assembled retractor 30 (FIGS. 2, 3 and 6). The guidewire 20 is threaded through the channel 50 formed in the body of the retractor 35, until the proximal end of the guidewire 21 emerges through the hole 47 in the cap 40 at the proximal end of the retractor 41 (FIG. 6). The retractor 30 is then slowly advanced along the guidewire 20 and into the patient's body, until resistance is felt. This resistance indicates that the distal tip of the retractor 37 is contacting the inflated balloon 24 in the femoral artery 10. The distal tip of the retractor 37 therefore will be properly located at the site of the puncture in the femoral artery 25, as is shown in FIG. 6.

In a preferred embodiment, the guidewire 20 used in conjunction with the femoral artery closure retractor 30 has a marking 27 on it which also helps to indicate when the retractor 30 has been properly positioned (FIG. 6). This marking 27 preferably consists of a tiny bead or colored line on the guidewire 20. The marking on the guidewire 27 is placed proximal of the proximal end of the balloon 26. The length of the retractor 30 is measured, and the marking 27 is made at least that same length in a proximal direction on the guidewire 20, measured from the proximal end of the balloon 26. Thus, when the retractor 30 is advanced over the guidewire 20 and resistance is felt, the physician checks to see if the marking on the guidewire 27 has emerged through the proximal end of the retractor 41, as is illustrated in FIG. 6. If the marking 27 is not yet visible, the physician must advance the retractor 30 further to ensure that it contacts the femoral artery puncture site 25.

Once the retractor 30 is properly positioned within the patient's body, the surgical clip applicator 70 or other method of closing the puncture wound 25 is used. The cap 40 on the retractor 30 is first removed from the body by unscrewing (FIG. 3). The proximal end of the guidewire 21 emerging from the proximal end of the retractor 41 is threaded through the guide 80 located on the outer surface of the applicator 70, as illustrated in FIG. 7. The wings on the surgical clip applicator 77a, 77b are inserted into the hole 90 formed at the proximal end of the body of the retractor 39, by lining up the wings 77a, 77b on the applicator 30 with the grooves 65 located on the inner surface 67 of the retractor body halves 35a, 35b (FIGS. 7 and 8). The wings on the clip applicator 77a, 77b are sized to fit within the grooves 65 of the retractor 30, as is best illustrated in FIG. 8. The clip applicator 70 is then advanced, which causes the two halves of the body of the retractor 35a, 35b to separate, as shown in FIG. 7. As the two halves 35a, 35b separate, the patient's tissue is displaced laterally, allowing better access to the puncture site 25 in the femoral artery 10 below the overlying tissues. The clip applicator 70 is advanced through the retractor 30 until the stop on the applicator 85 contacts the proximal end of the retractor 39. At this time, the balloon on the guidewire 24 or catheter is deflated, and the catheter and/or guidewire 20 is removed from the patient. The surgical clips located at the distal tip of the clip applicator 75 are applied to the puncture wound 25, using the method well known to those of ordinary skill in the art. Once the femoral artery puncture wound 25 is closed, the clip applicator 70 and retractor 30 are removed from the patient.

Referring now to FIGS. 9–16, the method of using the alternate embodiment of the retractor 100 in conjunction with the dilator 150 and surgical clip applicator assembly 130 to localize and close the femoral artery puncture wound is now described. As described above, following completion of the angioplasty or angiography, the catheter used during the procedure is removed from the patient's body, leaving only the guidewire threaded into the femoral artery. If desired, before the retractor-dilator assembly 101 (FIG. 13) is used, a standard dilator of a smaller diameter than that 150 incorporated into the retractor-dilator assembly 101 can be fed onto the proximal end of the guidewire and advanced down the guidewire and into the artery. This preliminary step dilates the overlying tissue if necessary, making it easier to subsequently pass the larger retractor-dilator assembly 101 through the surrounding tissue.

If the tissue has been dilated as above, the smaller bore standard dilator is first removed. The proximal end of the guidewire 144 is first inserted into the distal channel 160 (FIG. 11) of the dilator 150. The dilator 150 has been previously inserted through the internal channel of the retractor 100, and the retractor 100 mounted on the dilator 150 such that the distal tip 112 comes to rest in the notch 152 on the distal tip of the dilator 150. The Y-connector 156 is then attached to the proximal end of the dilator 150 and a syringe 158 attached to one of the ports of the connector 156. The retractor-dilator assembly 101 is then advanced over the guidewire 144 into the patient's body.

While the retractor-dilator assembly 101 is advanced into the patient's body, suction is continuously applied via the syringe 158 or other means of negative pressure (FIG. 13) to the dilator 150. At the moment the indicator holes 154 enter the lumen of the femoral artery, blood is aspirated into the syringe 158, indicating that the dilator 150 has been inserted through the puncture site into the femoral artery. Thus, the distal tip of the retractor 112, still buried within the notch 152 in the dilator 150, is located just proximal or outside the artery wall at the site of the puncture wound and the indicator holes 154 in the dilator 150 are located just distal or inside the artery lumen.

Alternatively, the dilator 150 includes a pressure sensor (not shown) such as a fiber optic pressure sensor, near its distal tip. The sensor is preferably mounted to the outside wall of the dilator 150. In a preferred embodiment, a transducer-tipped pressure monitoring catheter, such as the Camino Catheter available from Camino Laboratories, San Diego, Calif., is used. The pressure sensor, mounted on the outside of the dilator 150, is inserted over the guidewire 144 and into the femoral artery. The pressure sensor, in conjunction with a pressure monitoring system, will indicate an increase in pressure when it is inserted into the femoral artery. At that point, the advancement of the retractor 100 is stopped, such that the distal tip of the retractor 112 is located just proximal the artery wall 10 at the site of the puncture wound. This allows the physician to properly locate the site of the femoral artery puncture wound in the patient.

Once the dilator 150 and retractor 100 are in proper position, the cap 104 is removed from the retractor 100 and the two halves 102a, 102b of the retractor body are separated slightly (FIG. 10) by loosening the set screws 120a, 120b and sliding the two halves 102a, 102b of the retractor laterally away from one another. This causes the distal tips 112 of two halves 102a, 102b to emerge from the notch 152 in the dilator 150 (FIG. 11) and straddle the puncture site. The set screws 120a, 120b, are then tightened to hold the two halves 102a, 102b of the retractor 100 in this separated position. While pressing the retractor 100 down against the outer wall of the femoral artery, the dilator 150 is withdrawn, leaving only the retractor 100 and the guidewire 144 in position at the site of the puncture wound in the artery.

To close the wound, the retractor 100 must be retracted far enough to allow the surgical clip applicator assembly 130 to access the puncture site. Upon loosening the set screws 120a, 120b, the two halves 102a, 102b of the retractor are further separated by applying pressure on the retractor pin handle 116c (FIGS. 9–10). When sufficiently retracted, the set screws 120a, 120b on the retractor assembly 100 are tightened to maintain the proper distance between the retractor halves. If necessary, a separate retractor, having a thickness suited for sliding within the grooves 126 in each half 102a, 102b of the retractor body, and a width equal to that of the winged guide plate 138 (FIG. 14) of the surgical clip applicator guide assemble 134, can be used to open the retractor body to the proper distance.

In an alternate preferred embodiment illustrated in FIG. 17, the modified dilator 150 having a double-sleeved inflatable balloon 170 removably attached to the distal end of the dilator 151, just proximal the indicator hole 154, is used. The inner and outer sleeves of the double sleeved balloon 170 are detachable when moved laterally away from each other. The balloon dilator apparatus 175 is inserted over the guidewire 144 into the patient's body. As described above, as the balloon-dilator apparatus 175 is advanced, negative pressure is applied to the system via the syringe or other source. The advance of the balloon-dilator apparatus 175 is stopped as soon as blood is aspirated. The double-sleeved balloon 170 is then inflated to form a tunnel 176 between the femoral artery puncture wound and the surface of the patient's body, as illustrated in FIG. 18.

The double-sleeved balloon 170 advantageously prevents the femoral artery closure retractor 100 from entering the femoral artery 10 and damaging it. The cylindrical shape of the retractor's distal end 100 also prevents the retractor from entering the artery 10. Should the deflated balloon 170 be advanced into the femoral artery 10, the process of inflating the balloon 170 will pull the balloon 170 out of the artery 10, thereby safely creating a tunnel 176 used to access the artery 10.

The balloon 170 is preferably angled at its distal end 172 to allow the balloon 170 to "fit" the femoral artery 10, as shown in FIGS. 17–19.

Once the balloon 170 is inflated (FIG. 18) the retractor 100 is advanced between the two sleeves of the inflated balloon 170. The retractor 100 is positioned such that the distal tip of the retractor 112 reaches the distal, detachable junction of the two sleeves of the balloon 170, as shown in FIG. 19.

Once the retractor 100 is positioned between the two sleeves of the balloon 170, the two halves of the retractor 102a, 102b are moved laterally away from one another, as described above, which causes the two sleeves of the balloon 170 to detach. The inner sleeve 178 and the dilator 150 are removed from the patient, leaving the separated retractor 100 and the outer sleeve 180 of the balloon 170 in the patient.

The retractor 100 and the outer sleeve of the balloon 180 form an access tunnel 182 between the femoral artery puncture wound and the surface of the patient's body, as illustrated in FIG. 20. This tunnel 182 allows for the introduction of the wound closure device to seal the femoral artery puncture wound. The wound closure device can be inserted over the guidewire 144, which acts to guide the device to the site of the wound.

At this point, with the retractor providing access to the femoral artery, the proximal end of the guidewire 144 is inserted into the guidetube 136 on the surgical clip applicator assembly 130 and the wings on the guide plate are fitted within the grooves 126 of the opened retractor body 102 (FIGS. 14–16). The clip applicator assembly 130 can now be advanced toward the puncture wound, sliding within the grooves 126 in the retractor body 102, guided by the guidewire 144 passing through the guidetube 136 at the distal tip of the surgical clip applicator assembly 130. When the distal tip of the surgical clip applicator 130 has reached the outer wall of the femoral artery 10, at the site of the puncture wound, the surgeon withdraws the guidewire 144 from the patient's body and immediately deploys a surgical clip. A second clip can then be deployed a millimeter or two away from the first clip in order to ensure that the wound is closed.

In a preferred embodiment, just prior to closure of the puncture site, the flexible guidewire 144 used during the primary procedure is replaced with a commercially available variable stiffness guidewire that can become rigid at its distal end, forming a hook. The hooked distal end is preferably used to "hook" the bifurcation between the femoral and iliac arteries. Once hooked at the bifurcation, the guidewire cannot be pulled out of the patient's vasculature. Thus, when resistance is felt and the guidewire is hooked at the bifurcation, the guidewire is pulled back further and lifted slightly, causing the puncture wound to stretch into a linear slit and the edges of the wound are brought together, making it more amenable to closure by surgical clips.

The retractor can also be used with surgical staples or sutures. After the retractor is inserted into the patient's body and positioned within the puncture site as described above, the two halves of the retractor are manually separated, laterally displacing the tissues surrounding the puncture site 25. The retractor acts much like a dilator, gradually increasing the displacement of the overlying tissues, until the puncture wound is visible to the physician. The wound can then be closed using any acceptable means for wound closure, including surgical staples and sutures.

Although certain embodiments and examples have been used to illustrate and describe the present invention, it is intended that the scope of the invention not be limited to the specific embodiments set forth herein. The scope of the invention is to be defined by the claims which follow.

What is claimed is:

1. A device to facilitate the closure of wounds in the vasculature of a patient, comprising:
   a body portion having an externally threaded proximal end and a tapered distal end, wherein said body portion has two separate, halves, each of said halves having a flat internal surface with a groove therein, such that when said internal surfaces abut one another, said grooves form a channel extending completely through said body portion from said proximal end to said distal end;
   at least one connector pin extending from one of said halves of said body portion, said one connector pin dimensioned to be received within a correspondingly dimensioned bore defined in the other of said halves of said body portion to operatively connect said halves; and
   an internally threaded cap having a hole therethrough, said internal threads adapted to engage said externally threaded proximal end of said body portion, such that when said cap engages said body portion, said hole is positioned directly above said channel in said body portion.

2. The device of claim 1, further comprising at least one handle located on said proximal end of said body portion and extending laterally from said body portion.

3. The device of claim 1, wherein said body portion and said cap are comprised of a biocompatible engineering polymer.

4. The device of claim 3, wherein said polymer is selected from the group consisting of polypropylene, polyethylene, or polyterephthalate.

5. The device of claim 1, wherein said body portion and said cap are comprised of an elastomer.

6. The device of claim 1, wherein said body portion and said cap are comprised of a metal.

7. The device of claim 1, wherein said body portion and said cap are comprised of stainless steel.

8. The device of claim 1, further comprising a guidewire, wherein said guidewire can be inserted through said channel in said body portion and through said hole in said cap.

9. The device of claim 8, wherein said guidewire has an inflatable balloon attached thereto.

10. A system for facilitating the closure of wounds in the vasculature of a patient, comprising:
    a retractor comprising a body portion having an externally threaded proximal end and a tapered distal end, wherein said body portion has two separate halves, each of said halves having a flat internal surface with a groove therein, such that when said internal surfaces abut one another, said grooves form a channel extending completely through said body portion from said proximal end to said distal end; and an internally threaded cap having a hole therethrough, said internal threads adapted to engage said external threads on said body portion, such that when said cap engages said body portion, said hole is positioned directly above said channel in said body portion;
    a guidewire having an inflatable balloon attached thereto, wherein said guidewire can be inserted through said channel in said body portion and through said hole in said cap; and
    a surgical clip applicator having a distal end, wherein said distal end of said applicator has two laterally protruding wings attached, said wings being adapted to fit within the channel in said body portion of said retractor.

11. The system of claim 10, wherein said surgical clip applicator further comprises a guide attached to said distal end of said applicator and extending laterally therefrom, wherein said guide is adapted to receive said guidewire therethrough.

12. A method for facilitating the closure of wounds in the vasculature of a patient, comprising the steps of:
    inserting a guidewire having a proximal end and a distal end and an inflatable balloon into said vasculature through said wound, until said distal end of said guidewire is within the vasculature and the proximal end remains outside the patient's body;
    inflating said inflatable balloon;
    withdrawing said proximal end of said guidewire from said patient's body until said inflated balloon is located in said vasculature at said wound;
    inserting the proximal end of said guidewire into a distal end of a retractor comprising a body portion having an externally threaded rounded proximal end, wherein said body portion has two separate halves, each of said halves having a flat internal surface with a groove therein, such that when said internal surfaces abut one another, said grooves form a channel extending completely through said body portion from said proximal end to said distal end; and an internally threaded cap having a hole therethrough, said internal threads adapted to engage said external threads on said body portion, such that when said cap engages said body portion, said hole is positioned directly above said channel in said body portion, until said proximal end of said guidewire emerges through said hole in said cap;
    advancing said retractor along said guidewire and into said patient's body until said distal tip of said retractor contacts said inflated balloon;
    removing said cap from said body portion of said retractor;
    separating said two halves of said retractor until said wound is visible;
    removing said guidewire from said patient's body; and
    closing said wound.

13. The method of claim 12, wherein said closing step comprises a method selected from the group consisting of clipping, stapling, and suturing said wound.

14. The method of claim 12, further comprising the steps of inserting a surgical clip applicator into said retractor body portion after said cap is removed and advancing said clip applicator through said channel in said body portion until said applicator contacts said wound, and wherein said closing step comprises applying at least one surgical clip to said wound.

15. The method of claim 12, further comprising the step of deflating said balloon and withdrawing said guidewire from said patient's body prior to said closing step.

16. A method for facilitating the closure of wounds in the vasculature in a patient's body, comprising the steps of:
    inserting a guidewire having a proximal end and a distal end into said vasculature through said wound, until said distal end of said guidewire is within the vasculature and the proximal end remains outside the patient's body;

inserting a catheter having a proximal end and a distal end and having an inflatable balloon attached at said distal end, into said vasculature over said guidewire until said distal end is within said artery and said proximal end remains outside said patient's body;

inflating said inflatable balloon;

withdrawing said catheter from said patient's body until said inflated balloon is located in said vasculature at said wound;

inserting the proximal end of said guidewire into a distal end of a retractor comprising a body portion having an externally threaded rounded proximal end, wherein said body portion has two separate halves, each of said halves having a flat internal surface with a groove therein, such that when said internal surfaces abut one another, said grooves form a channel extending completely through said body portion from said proximal end to said distal end; and an internally threaded cap having a hole therethrough, said internal threads adapted to engage said external threads on said body portion, such that when said cap engages said body portion, said hole is positioned directly above said channel in said body portion; until said proximal end of said guidewire emerges through said hole in said cap;

advancing said retractor along said guidewire and into said patient's body until said distal tip of said retractor contacts said inflated balloon;

removing said cap from said body portion of said retractor;

separating said two halves of said retractor until said wound is visible; and removing said guidewire from said patient's body; and closing said wound.

17. The method of claim 16, wherein said closing step is a method selected from the group consisting of clipping, stapling, and suturing said wound.

18. The method of claim 16, further comprising the steps of inserting a surgical clip applicator into said retractor body portion after said cap is removed and advancing said clip applicator through said channel in said body portion until said applicator contacts said wound, and wherein said closing step comprises applying at least one surgical clip to said wound.

19. The method of claim 16, further comprising the step of deflating said balloon and withdrawing said catheter and said guidewire from said patient's body prior to said closing step.

20. A device to facilitate the closure of wounds in the vasculature of a patient, comprising:

a body portion having an externally threaded proximal end and a distal end, wherein said body portion has two separate halves, each of said halves having a flat internal surface with a groove therein, such that when said internal surfaces abut one another, said grooves form a channel extending completely through said body portion from said proximal end to said distal end;

a collar portion distal the externally threaded proximal end comprising at least one guide passage which traverses one half of said body portion;

at least one pin extending from one half of said body portion and insertable into said guide passage in the other half of said body portion; and an internally threaded annular cap, said internal threads adapted to engage said external threads on said body portion.

21. The device of claim 20, further comprising a handle extending laterally from said pin.

22. The device of claim 20, wherein device is comprised of a biocompatible engineering polymer.

23. The device of claim 22, wherein said polymer is selected from the group consisting of polypropylene, polyethylene, or polyterephthalate.

24. The device of claim 20, wherein said device is comprised of an elastomer.

25. The device of claim 20, wherein said device is comprised of a metal.

26. The device of claim 20, wherein said device is comprised of stainless steel.

27. The device of claim 20, further comprising at least one set screw hole in said collar portion at a right angle to said guide passage, and at least one set screw insertable into said set screw hole.

28. The device of claim 20, wherein said distal tip is tapered.

29. The device of claim 20, wherein said distal tip is cylindrical.

30. The device of claim 20, further comprising a hollow dilator having an open proximal end and an open distal end adapted to receive a guidewire therethrough, wherein said dilator can be inserted through said channel in said body portion and through said annular cap.

31. The device of claim 30, wherein said distal tip is tapered and wherein said dilator further comprises a notch near said distal end sized to receive the tapered distal end of the body portion of the device.

32. The device of claim 30, wherein said dilator has at least one indicator hole through a side wall located distal said notch.

33. The device of claim 30, wherein said dilator further comprises a pressure sensor mounted on an outside wall of said dilator.

34. The device of claim 20, further comprising a guidewire, wherein said guidewire can be inserted through said hollow dilator.

35. The device of claim 20, further comprising a hollow dilator having an open proximal end and an open distal end adapted to receive a guidewire therethrough, wherein said dilator can be inserted through said channel in said body portion and through said annular cap, said hollow dilator having a double-sleeved inflatable balloon mounted on its distal end.

36. The device of claim 35, wherein said dilator further comprises at least one indicator hole at its distal end through a side wall, and wherein said double-sleeved inflatable balloon is mounted approximately 1.5 mm proximal said indicator hole.

37. A system for facilitating the closure of wounds in the vasculature of a patient, comprising:

a retractor comprising a body portion having an externally threaded proximal end and a distal end, wherein said body portion has two separate halves, each of said halves having a flat internal surface with a groove therein, such that when said internal surfaces abut one another, said grooves form a channel extending completely through said body portion from said proximal end to said distal end; a collar portion distal the externally threaded proximal end comprising at least one guide passage which traverses both halves of said body portion; at least one pin insertable into said guide passage; and an internally threaded annular cap, said internal threads adapted to engage said external threads on said body portion;

a hollow dilator having an open proximal end and an open distal end adapted to receive a guidewire therethrough, wherein said dilator can be inserted through said channel in said body portion and through said annular cap; and a guidewire insertable through said dilator.

38. The system of claim 37, further comprising a guide assembly adapted for attachment to a distal end of a surgical clip applicator, said assembly comprising a guide plate which is reversibly attachable to a guide body having an attached guide tube sized to receive a guidewire therethrough, wherein said guide plate has two laterally protruding wings attached, said wings being adapted to fit within the channel in said body portion of said retractor.

39. The system of claim 37, further comprising a source of negative pressure attached to said open proximal end of said dilator.

40. The system of claim 39, wherein said source of negative pressure comprises a syringe.

41. The system of claim 37, further comprising a Y-connector having a plurality of ports attached to the proximal end of the dilator at one of said ports.

42. The system of claim 41, further comprising a source of negative pressure attached to one of the ports of said Y-connector.

43. A method for facilitating the closure of a wound in the vasculature of a patient, comprising the steps of:

inserting a proximal end of a hollow dilator having a notch formed near its distal end into a distal end of a retractor comprising a body portion having an externally threaded rounded proximal end, and a tapered distal end, wherein said body portion has two separate halves, each of said halves having a flat internal surface with a groove therein, such that when said internal surfaces abut one another, said grooves form a channel extending completely through said body portion from said proximal end to said distal end; and an internally threaded annular cap, said internal threads adapted to engage said external threads on said body portion, such that when said cap engages said body portion, said proximal end of said hollow dilator pass through said channel in said body portion and out said annular cap;

mounting said retractor on said hollow dilator such that said distal tapered end is positioned within said notch;

inserting a guidewire having a proximal end and a distal end into said vasculature through said wound, until said distal end of said guidewire is within the vasculature and the proximal end remains outside the patient's body;

inserting the proximal end of said guidewire into said distal end of said hollow dilator until the proximal end of the guidewire emerges through said proximal end of said dilator;

advancing said dilator and retractor along said guidewire and into said patient's body, while providing a source of negative pressure on said dilator until blood is drawn into said dilator from said vasculature;

removing said cap from said body portion of said retractor;

separating said two halves of said retractor;

removing said guidewire and said dilator from said patient's body; and closing said wound.

44. The method of claim 43, wherein said closing step comprises a method selected from the group consisting of clipping, stapling, and suturing said wound.

45. The method of claim 43, further comprising the steps of attaching to a distal end of a surgical clip applicator a guide having laterally extending wings, inserting said wings into said retractor body portion after said cap is removed and advancing said clip applicator through said channel in said body portion until said applicator contacts said wound, and wherein said closing step comprises applying at least one surgical clip to said wound.

46. The method of claim 45, wherein said guide further comprises a guidetube for receiving said guidewire, and said method further comprises inserting the proximal end of the guidewire through said guidetube and advancing said applicator over said guidewire and through said channel in said body portion until said applicator contacts said wound.

47. A method for facilitating the closure of a wound in the vasculature of a patient, comprising the steps of:

inserting a guidewire having a proximal end and a distal end into said vasculature through said wound, until said distal end of said guidewire is within the vasculature and the proximal end remains outside the patient's body;

inserting the proximal end of said guidewire into a distal end of a hollow dilator having a double-sleeved balloon having an inner sleeve and an outer sleeve mounted on said distal end;

advancing said dilator over said guidewire until it reaches said wound;

inflating said double-sleeved balloon;

inserting said proximal end of said guidewire into a distal end of a retractor comprising a body portion having an externally threaded rounded proximal end, and a distal end, wherein said body portion has two separate halves, each of said halves having a flat internal surface with a groove therein, such that when said internal surfaces abut one another, said grooves form a channel extending completely through said body portion from said proximal end to said distal end; and an internally threaded annular cap, said internal threads adapted to engage said external threads on said body portion, such that when said cap engages said body portion, said proximal end of said hollow dilator pass through said channel in said body portion and out said annular cap;

mounting said retractor on said hollow dilator until said distal end is positioned between the inner and outer sleeves of the double-sleeved balloon;

removing said cap from said body portion of said retractor;

separating the two halves of said retractor and removing said dilator and the inner sleeve of said double-sleeved balloon therethrough; and closing said wound.

48. The method of claim 47, wherein said closing step comprises a method selected from the group consisting of clipping, stapling, and suturing said wound.

49. The method of claim 47, further comprising the steps of attaching to a distal end of a surgical clip applicator a guide having laterally extending wings, inserting said wings into said retractor body portion after said cap is removed and advancing said clip applicator through said channel in said body portion until said applicator contacts said wound, and wherein said closing step comprises applying at least one surgical clip to said wound.

50. The method of claim 47, wherein said guide further comprises a guidetube for receiving said guidewire, and said method further comprises inserting the proximal end of the guidewire through said guidetube and advancing said applicator over said guidewire and through said channel in said body portion until said applicator contacts said wound.

51. The method of claim 47, further comprising providing a source of negative pressure on said dilator until blood is drawn into said dilator from said vasculature, during said advancing of said dilator over said guidewire.

52. A device to facilitate the closure of wounds in the vasculature of a patient, comprising:
- a body portion having an externally threaded proximal end and a tapered distal end, wherein said body portion has two separate halves operatively connected to each other through cooperative reception of a connecting pin extending from one of the halves of the body portion and a cooperating slot which receives the connecting pin, each of said halves having a flat internal surface with a groove therein, such that when said internal surfaces abut one another, said grooves form a channel extending completely through said body portion from said proximal end to said distal end; and
- an internally threaded cap having a hole therethrough, said internal threads adapted to engage said externally threaded proximal end of said body portion, such that when said cap engages said body portion, said hole is positioned directly above said channel in said body portion; and
- a guidewire, wherein said guidewire can be inserted through said channel in said body portion and through said hole in said cap.

53. The device of claim 52, wherein said guidewire has an inflatable balloon attached thereto.

54. A device to facilitate the closure of wounds in the vasculature of a patient, comprising:
- a body portion having an externally threaded proximal end and a distal end, wherein said body portion has two separate halves, each of said halves having a flat internal surface with a groove therein, such that when said internal surfaces abut one another, said grooves form a channel extending completely through said body portion from said proximal end to said distal end;
- a collar portion distal the externally threaded proximal end comprising at least one guide passage which traverses one half of said body portion;
- at least one pin extending from one half of said body portion and insertable into said guide passage in the other half of said body portion;
- an internally threaded annular cap, said internal threads adapted to engage said external threads on said body portion; and
- and least one set screw hole in said collar portion at a right angle to said guide passage, and at least one set screw insertable into said set screw hole.

55. A device to facilitate the closure of wounds in the vasculature of a patient, comprising:
- a body portion having an externally threaded proximal end and a distal end, wherein said body portion has two separate halves, each of said halves having a flat internal surface with a groove therein, such that when said internal surfaces abut one another, said grooves form a channel extending completely through said body portion from said proximal end to said distal end;
- a collar portion distal the externally threaded proximal end comprising at least one guide passage which traverses one half of said body portion;
- at least one pin extending from one half of said body portion and insertable into said guide passage in the other half of said body portion;
- an internally threaded annular cap, said internal threads adapted to engage said external threads on said body portion; and
- a hollow dilator having an open proximal end and an open distal end adapted to receive a guidewire therethrough, wherein said dilator can be inserted through said channel in said body portion and through said annular cap.

56. The device of claim 55, wherein the distal end of the body portion is tapered and wherein said dilator further comprises a notch near said distal end sized to receive the tapered distal end of the body portion of the device.

57. The device of claim 55, wherein said dilator has at least one indicator hole through a side wall located distal said notch.

58. The device of claim 55, wherein said dilator further comprises a pressure sensor mounted on an outside wall of said dilator.

59. The device of claim 55, further comprising a guidewire, wherein said guidewire can be inserted through said hollow dilator.

60. The device of claim 55, wherein said hollow dilator has a double-sleeved inflatable balloon mounted on its distal end.

61. The device of claim 60, wherein said dilator further comprises at least one indicator hole at its distal end through a side wall, and wherein said double-sleeved inflatable balloon is mounted approximately 1.5 mm proximal said indicator hole.

62. A surgical retractor which comprises:
- an elongated body portion having proximal and distal ends and defining a longitudinal axis, the elongated body portion including at least two separate cooperating members operatively connected to each other and adapted for relative movement between an approximated position and a displaced position, each cooperating member having internal surfaces dimensioned to define a longitudinal passage extending through the elongated body portion for reception of surgical instrumentation, the elongated body portion having a distal tapered portion for facilitating entry into tissue;
- an end cap removably mounted to the proximal end of the elongated body portion, the end cap configured to retain the cooperating members in the approximated position wherein upon removal of the end cap from the elongated body portion the cooperating members may be displaced relative to each other to move to the displaced position thereof, and
- a locking member independent of the end cap for securing the cooperating members at desired relative positions between the approximated and displaced positions.

63. The surgical retractor according to claim 62 wherein the elongated body portion and the end cap include threaded portions, the threaded portions cooperating to mount the end cap to the elongated body portion.

64. The surgical retractor according to claim 62 wherein the end cap includes an opening in general alignment and in communication with the longitudinal passage of the elongated body portion.

65. The surgical retractor according to claim 62 including a connector extending between the cooperating members to operatively connect the cooperating members.

66. The surgical retractor according to claim 65 wherein at least one of the cooperating members is movable relative to the connector.

67. The surgical retractor according to claim 66 wherein the locking member is mounted to the one cooperating member, the locking member movable to engage the connector to secure the one cooperating member at a desired relative position.

68. The surgical retractor according to claim 65 wherein the connector is fixedly mounted to a first of the cooperating members and wherein a second of the cooperating members is movable relative to the first cooperating member and the connector.

69. The surgical retractor according to claim 68 wherein the locking member is mounted to the other second cooperating member and is positioned to selectively engage the connector to secure the cooperating members at the desired relative position.

70. A method for facilitating closure of an opening in a blood vessel where access to the opening is through a tissue passage extending through tissue overlying the blood vessel, comprising the steps of:

positioning a retractor at least partially within the tissue passage, the retractor including an elongated body having proximal and distal ends and defining a longitudinal axis, the elongated body having first and second body portions defining a longitudinal passage therebetween and being adapted for relative movement between an approximated position and a displaced position;

advancing the retractor through the tissue passage whereby the distal end thereof is proximal the opening in the blood vessel;

moving at least the first body portion relative to the second body portion to cause the elongated body to assume the displaced position whereby the body portions retract the tissue defining the tissue passage to increase a dimension of the tissue passage to facilitate access to the opening; and closing the opening in the blood vessel while the retractor is partially positioned within the tissue passage.

71. The method according to claim 70 wherein the step of closing including introducing a wound closure device through the tissue passage between the first and second body portions, and actuating the wound closure device.

72. The method according to claim 71 including the step of introducing a guide wire within the tissue passage such that a distal end thereof extends through the opening within the blood vessel.

73. The method according to claim 72 wherein the step of advancing includes positioning the guide wire within the longitudinal passage and guiding the retractor along the guide wire.

74. The method according to claim 73 wherein the guide wire includes an inflatable balloon adjacent the distal end thereof and further including the steps of:

inflating said inflatable balloon; and moving said guide wire such that said inflatable balloon engages an inner surface of the blood vessel adjacent the opening.

75. The method according to claim 74 wherein the step of advancing the retractor includes advancing the retractor such that the distal end of the elongated body contacts the inflated balloon.

76. The method according to claim 73 wherein the step of closing includes advancing the would closure device along the guide wire to a position adjacent the opening in the blood vessel.

77. The method according to claim 76 wherein the wound closure device includes a guide having a guide wire passage for reception of the guide wire and wherein the step of advancing the wound closure device includes positioning the guide wire within the guide wire passage of the guide.

78. The method according to claim 70 wherein the retractor includes a dilator mounted within the longitudinal passage of the elongated body and wherein the step of advancing includes moving the retractor and dilator through the tissue passage.

* * * * *